United States Patent [19]

Saotome et al.

[11] Patent Number: 4,882,489

[45] Date of Patent: Nov. 21, 1989

[54] RADIATION IMAGE RECORDING AND READ-OUT APPARATUS

[75] Inventors: Shigeru Saotome; Masamitsu Ishida, both of Kanagawa, Japan

[73] Assignee: Fuji Photo Film Co., Ltd., Kanagawa, Japan

[21] Appl. No.: 183,806

[22] Filed: Apr. 20, 1988

[30] Foreign Application Priority Data

Apr. 20, 1987 [JP] Japan .................................. 62-96715

[51] Int. Cl.⁴ .............................................. G03B 42/02
[52] U.S. Cl. ............................... 250/327.2; 250/484.1
[58] Field of Search .................. 250/327.2 C, 327.2 J, 250/484.1 B

[56] References Cited

U.S. PATENT DOCUMENTS

| | | | |
|---|---|---|---|
| 3,777,163 | 4/1973 | Aubin et al. | 250/493.1 |
| 4,258,264 | 3/1981 | Kotera et al. | 250/484.1 |
| 4,276,473 | 6/1981 | Kato et al. | 250/327.2 |
| 4,315,318 | 2/1982 | Kato et al. | 382/6 |
| 4,387,428 | 6/1983 | Ishida et al. | 364/413.13 |
| 4,400,619 | 8/1983 | Kotera et al. | 250/327.2 |
| 4,762,999 | 8/1988 | Saotome et al. | 250/327.2 |

FOREIGN PATENT DOCUMENTS

| | | | |
|---|---|---|---|
| 0181520 | 10/1985 | European Pat. Off. | 250/327.2 |
| 0220629 | 10/1986 | European Pat. Off. | 250/327.2 |
| 56-11395 | 2/1981 | Japan | 250/327.2 |
| 61-278843 | 12/1986 | Japan | 250/327.2 |

Primary Examiner—Constantine Hannaher
Attorney, Agent, or Firm—Sughrue, Mion, Zinn, Macpeak & Seas

[57] ABSTRACT

A radiation image recording and read-out apparatus comprises a radiation source for irradiating a radiation toward an object, a recording and read-out unit for recording a radiation image of the object on a stimulable phosphor sheet at an image recording position and reading the radiation image therefrom, and a movement system for moving the recording and read-out unit and the radiation source so that the stimulable phosphor sheet at the image recording position approximately satisfies the linear rule and the geometric rule with respect to the radiation source around an arbitrary tomographic layer. The recording and read-out unit is provided with a case having a size nearly equal to a single image recording area on the stimulable phosphor sheet, an image recording section, an image read-out section provided in the case for reading the radiation image from the stimulable phosphor sheet by exposure to stimulating rays, and an erasing section provided in the case.

5 Claims, 9 Drawing Sheets

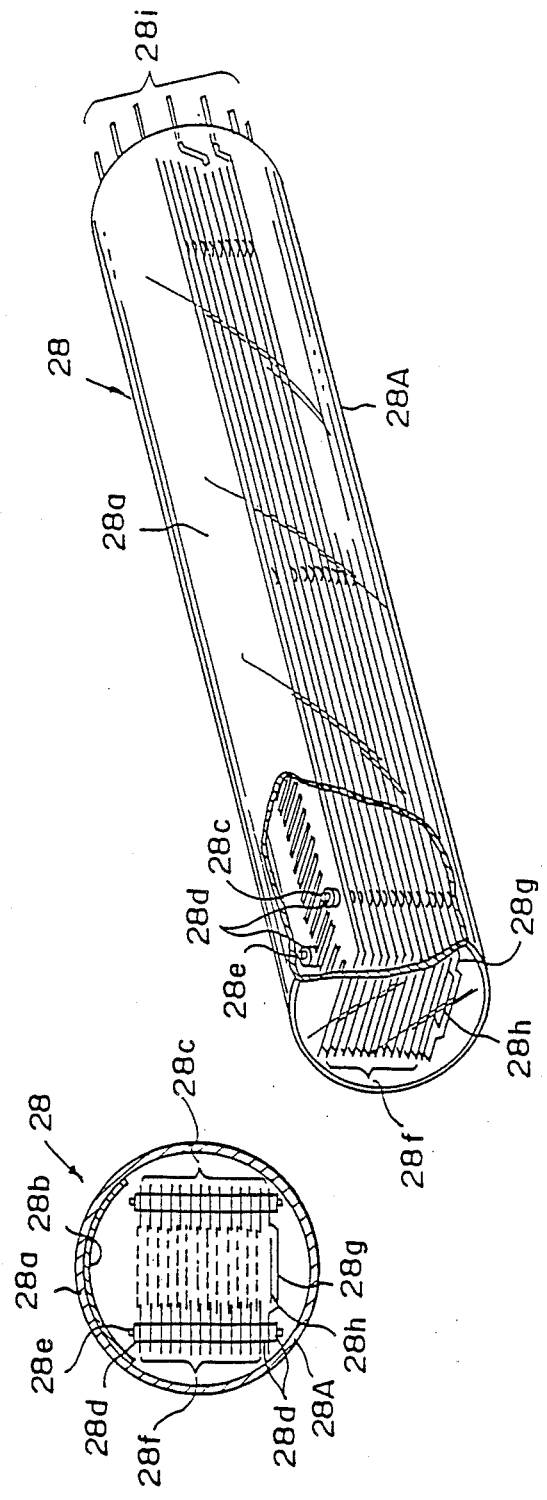

RADIATION IMAGE RECORDING AND READ-OUT APPARATUS

BACKGROUND OF THE INVENTION

1. Field of the Invention

This invention relates to a radiation image recording and read-out apparatus for recording a radiation image of an object, and reading out the radiation image to obtain electric image signals. This invention particularly relates to a radiation image recording and read-out apparatus wherein a tomographic image of an object is recorded on a stimulable phosphor sheet capable of storing the radiation energy.

2. Description of the Prior Art

As a method of obtaining a tomographic image of a desired tomographic layer of an object such as the human body, tomography has heretofore been known. In the tomography, a radiation source such as an X-ray tube and a radiographic film are positioned with the object intervening therebetween and are moved relative to each other at the time of irradiation of radiation around an arbitrary tomographic layer of the object so that the linear rule (specifying that the focal point of the radiation source, a point on the tomographic layer, and a point on the radiographic film be positioned on a straight line) and the geometric rule (specifying that the ratio of the distance between the focal point of the radiation source and the tomographic layer to the distance between the tomographic layer and the radiographic film be maintained constant) are satisfied. In this manner, only an image of a desired tomographic layer is formed on the radiographic film, and images of the other tomographic layers of the object are blurred. As a result, a radiation image of only the desired tomographic layer of the object is obtained. In the tomography, it is only necessary that the linear rule and the geometric rule be satisfied, and movements of the radiation source and the radiographic film may be carried out along any path, for example, a linear path, a circular path, an elliptic path, a spiral path, or a hypocycloidal path.

The applicant proposed a radiation image recording and read-out apparatus which can carry out tomography efficiently as disclosed in Japanese Unexamined Patent Publication No. 61(1986)-99138 (U.S. Pat. No. 4,762,999). Basically, the proposed radiation image recording and read-out apparatus comprises:

(i) a radiation source such as an X-ray tube for irradiating a radiation toward an object, (ii) a circulation and conveyance means for conveying at least one stimulable phosphor sheet for recording a radiation image thereon along a predetermined circulation path, (iii) an image recording section for disposing the stimulable phosphor sheet at an image recording position exposed to the radiation passing through the object, and recording a radiation image of the object on the stimulable phosphor sheet at the image recording position, (iv) a movement means for moving the stimulable phosphor sheet and the radiation source at the image recording section relative to each other around an arbitrary tomographic layer of the object so that the linear rule and the geometric rule are approximately satisfied, (v) an image read-out section disposed on the circulation path and provided with a means for irradiating the stimulating rays to the stimulable phosphor sheet carrying the radiation image stored thereon, and a photoelectric read-out means for detecting light emitted by the stimulable phosphor sheet exposed to the stimulating rays to obtain image signals, and (vi) an erasing section disposed on the circulation path for, prior to the next image recording on the stimulable phosphor sheet for which the image read-out has been carried out at the image read-out section, having the stimulable phosphor sheet release the radiation energy remaining on the stimulable phosphor sheet.

The stimulable phosphor sheet will now be described below. When certain kinds of phosphors are exposed to a radiation such as X-rays, $\alpha$-rays, $\beta$-rays, $\gamma$-rays, cathode rays or ultraviolet rays, they store a part of the energy of the radiation. Then, when the phosphor which has been exposed to the radiation is exposed to stimulating rays such as visible light, light is emitted by the phosphor in proportion to the stored energy of the radiation. A phosphor exhibiting such properties is referred to as a stimulable phosphor. The term "stimulable phosphor sheet" as used herein means a sheet-shaped recording material composed of the stimulable phosphor. In general, the stimulable phosphor sheet is composed of a substrate and a layer of the stimulable phosphor overlaid on the substrate. The stimulable phosphor layer comprises a binder and the stimulable phosphor dispersed therein. In the case where the stimulable phosphor layer is self-supporting, the stimulable phosphor layer itself can constitute the stimulable phosphor sheet. The stimulable phosphor sheet is described in detail in, for example, U.S. Pat. Nos. 4,258,264, 4,276,473, 4,315,318 and 4,387,428 and Japanese Unexamined Patent Publication No. 56(1981)-11395. In the case where the stimulable phosphor sheet is utilized, a radiation image can be recorded at a higher sensitivity, a higher resolution and less distortion than in the case where the radiographic film is used.

With the aforesaid radiation image recording and read-out apparatus, a radiation image of the object is stored on the stimulable phosphor sheet by moving the stimulable phosphor sheet and the radiation source relative to each other in the manner as mentioned. The stimulable phosphor sheet is then exposed to stimulating rays such as visible light which cause the stimulable phosphor sheet to emit light in proportion to the stored radiation energy, and the emitted light is detected photoelectrically. In this manner, electric image signals representing the radiation image which was stored on the stimulable phosphor sheet are obtained. By use of the electric image signals, a tomographic image of the object can be reproduced.

However, the radiation image recording and read-out apparatus having the aforesaid configuration wherein the stimulable phosphor sheet is circulated and conveyed along the circulation path and sequentially sent to the image recording section, the image read-out section and the erasing section, has the drawback that the apparatus becomes large. Also, with the aforesaid conventional radiation image recording and read-out apparatus, it is necessary to carry out transfer of the stimulable phosphor sheet between the circulation and conveyance means for the stimulable phosphor sheet and the means for moving the stimulable phosphor sheet relative to the radiation source. To satisfy this requirement, the mechanism becomes complicated and the apparatus becomes larger.

SUMMARY OF THE INVENTION

The primary object of the present invention is to provide a radiation image recording and read-out apparatus which enables efficient recording of a tomographic radiation image of an object and the read-out of the recorded image for obtaining electric image signals.

Another object of the present invention is to provide a radiation image recording and read-out apparatus which enables efficient recording of a tomographic radiation image of an object and which is small and light.

The radiation image recording and read-out apparatus in accordance with the present invention is characterized by, instead of conveying a stimulable phosphor sheet sequentially to an image recording section, an image read-out section and an erasing section along a circulation and conveyance path, providing a small recording and read-out unit containing a stimulable phosphor sheet and provided with the image recording, read-out and erasing functions, and moving the whole recording and read-out unit and a radiation source relative to each other so that the linear rule and the geometric rule are satisfied.

Specifically, the present invention provides a radiation image recording and read-out apparatus which comprises:

(i) a radiation source for irradiating a radiation toward an object, (ii) a recording and read-out unit provided with:

(a) a case for housing therein a stimulable phosphor sheet and having longitudinal and transverse dimensions approximately equal to the longitudinal and transverse dimensions of a single image recording area on said stimulable phosphor sheet, (b) an image recording section for holding said stimulable phosphor sheet in said case at an image recording position exposed to the radiation passing through said object, and having a radiation image of said object stored on said stimulable phosphor sheet, (c) an image read-out section provided in said case for exposing said stimulable phosphor sheet carrying said radiation image stored thereon to stimulating rays which cause said stimulable phosphor sheet to emit light in proportion to the stored radiation energy, and photoelectrically detecting the emitted light to obtain image signals, and (d) an erasing section provided in said case for releasing the radiation energy remaining on said stimulable phosphor sheet, for which the detection of said emitted light has been carried out, before the image recording is carried out on said stimulable phosphor sheet, and (iii) a movement means for moving said recording and read-out unit and said radiation source so that said stimulable phosphor sheet at said image recording position approximately satisfies the linear rule and the geometric rule with respect to said radiation source around an arbitrary tomographic layer.

With the radiation image recording and read-out apparatus in accordance with the present invention wherein tomography is carried out by moving the small recording and read-out unit containing the stimulable phosphor sheet and provided with the image recording, image read-out and erasing functions, the tomography can be carried out very efficiently. Also, with the radiation image recording and read-out apparatus in accordance with the present invention wherein the small recording and read-out unit is utilized and no mechanism for transfer of the stimulable phosphor sheet is necessary, the apparatus can be made markedly smaller and lighter than the conventional radiation image recording and read-out apparatus wherein the stimulable phosphor sheet is circulated and conveyed.

DESCRIPTION OF THE PREFERRED EMBODIMENTS

The present invention will hereinbelow be described in further detail with reference to the accompanying drawings.

Figure 1:
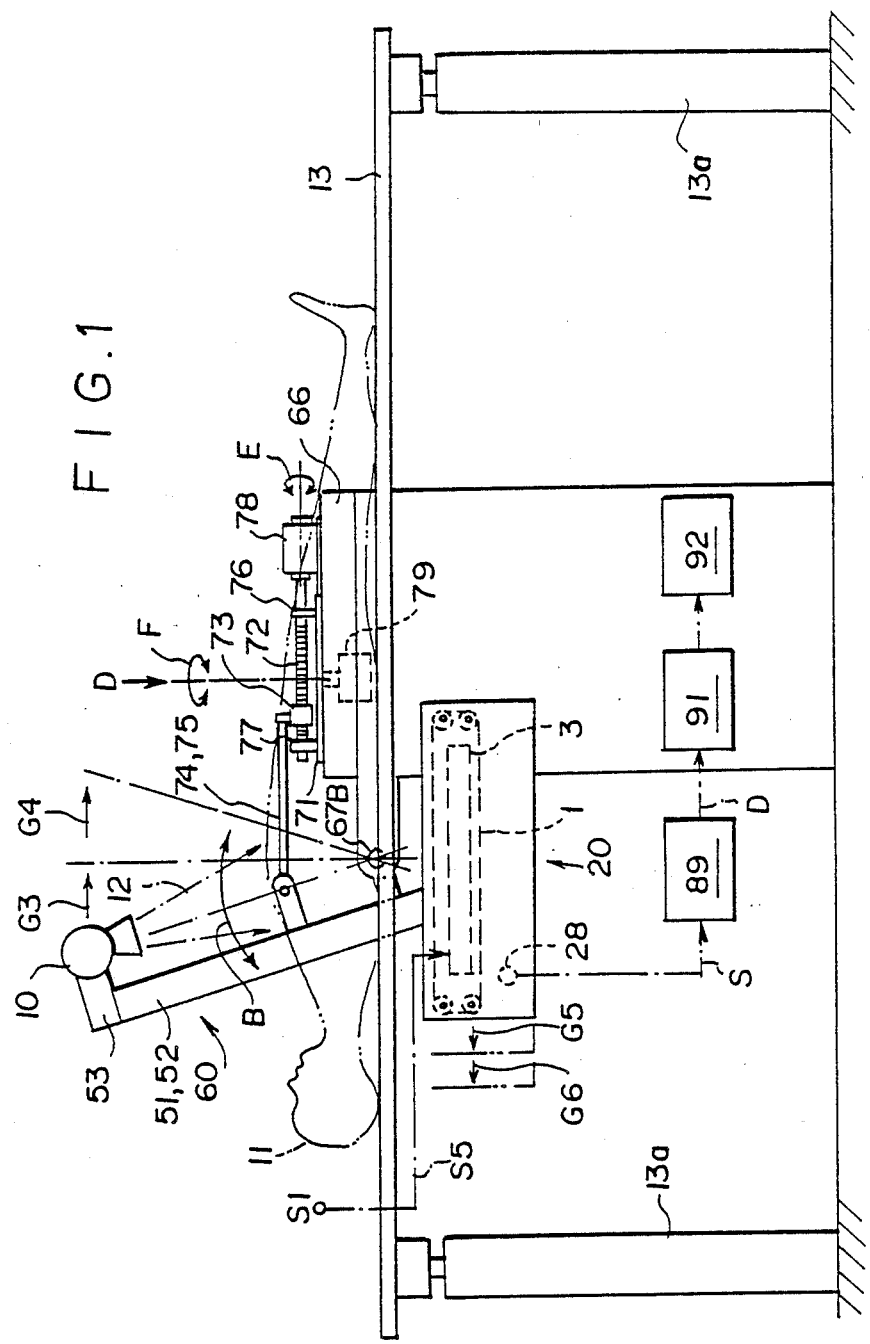
FIGS. 1 and 2 are a schematic elevational view and a schematic side view showing an embodiment of the radiation image recording and read-out apparatus in accordance with the present invention.
Figure 2:
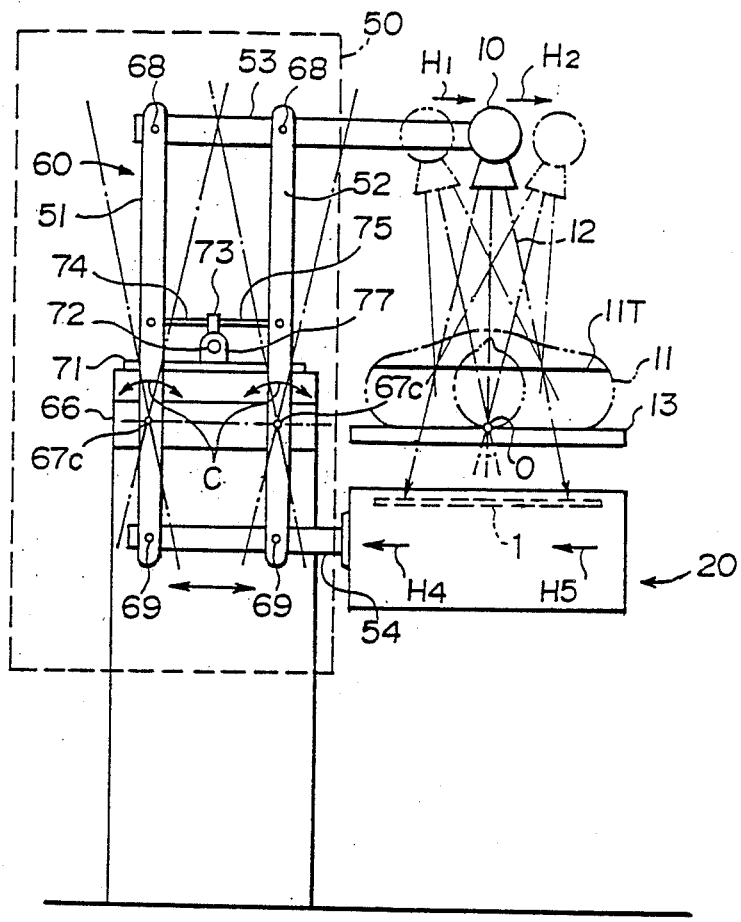

With reference to FIGS. 1 and 2, an embodiment of the radiation image recording and read-out apparatus in accordance with the present invention is provided with an image recording table 13 for supporting an object 11, a recording and read-out unit 20 provided at a position exposed to radiation 12 such as X-rays produced by a radiation source 10 constituted by an X-ray tube or the like and passing through the object 11, and a movement means 50 for moving the radiation source 10 so that the irradiation angle of the radiation 12 with respect to the object 11 changes, and for moving the recording and read-out unit 20.

First, the recording and read-out unit 20 will be described below with reference to FIGS. 4 and 5. An endless recording belt 1 provided with a stimulable phosphor layer approximately over the overall outer surface and thus formed as a stimulable phosphor sheet is applied around a first roller section 43 composed of rollers 41 and 42, and a second roller section 46 composed of rollers 44 and 45 spaced by a predetermined distance from the first roller section 43. The rollers 41, 42 and 44 are the driven rollers rotated as the recording belt 1 is moved, and the roller 45 is a drive roller coupled with a rotation shaft 48a of a motor 48 by a power transmission means 47 constituted by a belt, a chain or the like. As the drive roller 45 is rotated, the recording belt 1 is rotated and moved in the direction as indicated by the arrow in FIG. 4.

The case wherein an ordinary radiation image is to be recorded will first be described below. The object 11 is placed on the image recording table 13, and the radiation source 10 is activated. As a result, the radiation 12 passing through the object 11 impinges upon the recording belt 1, and a radiation image of the object 11 is stored on the stimulable phosphor layer of the recording belt 1. The distance between the roller sections 43 and 46 is nearly equal to the length of the single image recorded in this manner. Therefore, with a single recording step, the radiation image is stored over the overall area of the upper side part of the recording belt 1. Thus, in this embodiment, an image recording section 4 is formed between the upper rollers 41 and 44.

The recording belt 1 is maintained stationary as long as the image recording is being carried out. When the image recording is finished, a drive signal S1 is fed to a control circuit 3 in the recording and read-out unit 20, by way of example, automatically in synchronization with the operation of the radiation source 10. The motor 48 is thereby operated to rotate the drive roller 45, and the recording belt 1 is moved. In this manner, the image-recorded portion of the recording belt 1 is conveyed to an image read-out section 30 provided below the recording belt 1. A rotary encoder 39 is provided on a rotation shaft 48a of the motor 48, and the motor 48 is stopped at the time the rotary encoder 39 detects that the recording belt 1 has rotated one-half turn.

Figure 4:
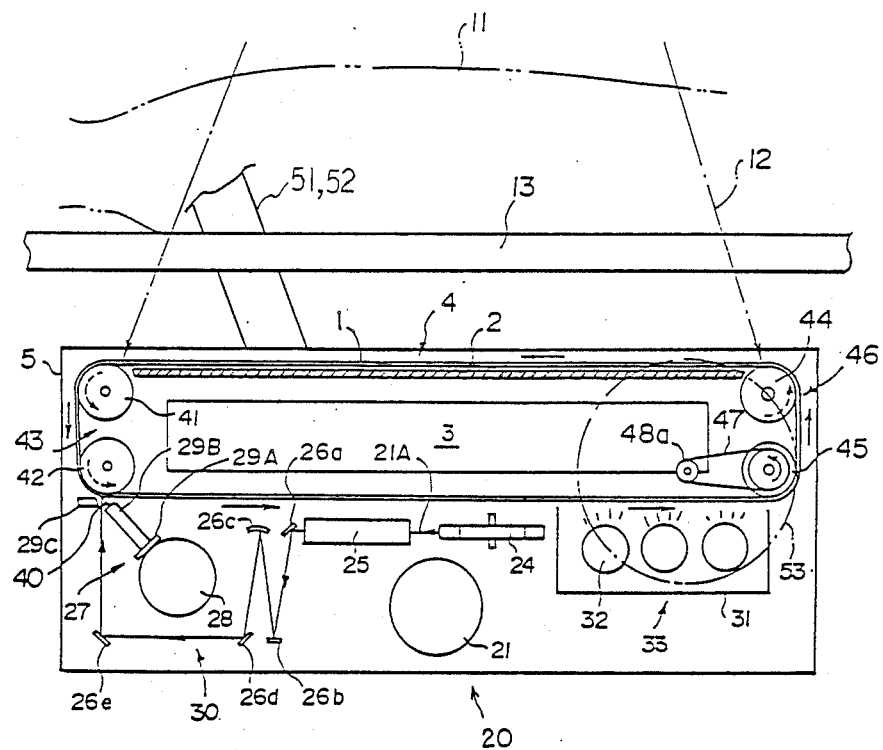
Figure 5:
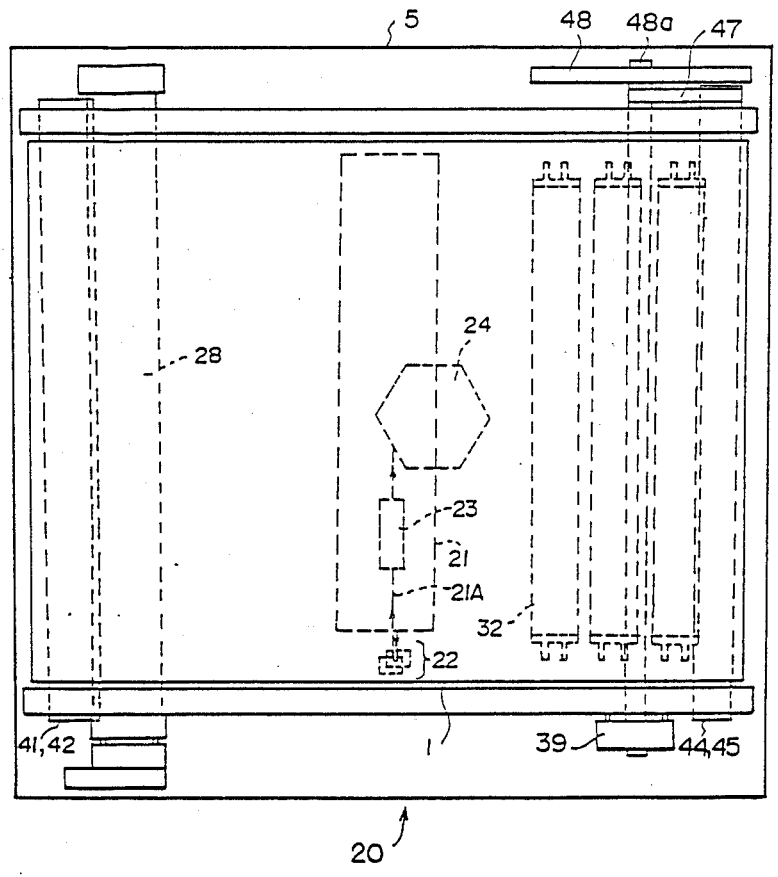

At the image read-out section 30, a stimulating ray source 21 constituted by a He-Ne laser or the like for producing stimulating rays 21A extends in the width direction of the recording belt 1, i.e. in the vertical direction in FIG. 5. Also, a rotating polygon mirror 24 is provided as a light deflector for scanning the stimulating rays 21A on the recording belt 1 in the width direction of the recording belt 1, i.e. in the main scanning direction. As shown in FIG. 5, the optical path of the stimulating rays 21A produced by the stimulating ray source 21 is changed by a mirror group 22, and then the stimulating rays 21A pass through a light input optical system 23 provided with a beam expander, a cylindrical lens or the like, and impinge upon the rotating polygon mirror 24. As shown in FIG. 4, the stimulating rays 21A reflected and deflected by the rotating polygon mirror 24 pass through a scanning optical system 25 composed of an fθ lens or the like, the optical path of the stimulating rays 21A is changed by mirrors 26a, 26b, 26c, 26d and 26e, and then the stimulating rays 21A impinge upon the recording belt 1 on the lower circumferential surface of the roller 42 and scans the recording belt 1 in the main scanning direction as mentioned above. The mirror 26c is a cylindrical mirror for converging the stimulating rays 21A only in a plane parallel to the drawing sheet in FIG. 4. In the aforesaid optical system, the mirror 26c and the cylindrical lens in the aforesaid light input optical system 23 prevent pitch nonuniformity of scanning lines from arising on the recording belt 1 even though axis deviation, mirror surface inclination or the like arises with the rotating polygon mirror 24. Simultaneously with the main scanning by the stimulating rays 21A, the recording belt 1 is moved by the drive roller 45 at a predetermined speed. Sub-scanning with the stimulating rays 21A is carried out in this manner, and the stimulating rays 21A are irradiated to nearly the overall surface of the image-recorded portion of recording belt 1.

As the recording belt 1 is exposed to the stimulating rays 21A, the exposed part of the recording belt 1 emits light 40 in an amount proportional to the stored radiation energy, and the emitted light 40 is detected by a photoelectric read-out means 27. In this embodiment, the photoelectric read-out means 27 comprises a long photomultiplier 28 having a light receiving face extending in the main scanning direction at least over the length of the main scanning line, a filter 29A closely contacted with the light receiving face of the photomultiplier 28 for selectively transmitting only the light 40 emitted by the recording belt 1 and preventing entry of the stimulating rays 21A reflected by the surface of the recording belt 1 to the photomultiplier 28, and a light guide member 29B provided on the filter 29A for guiding the light 40 emitted by the recording belt 1 to the photomultiplier 28. Also, a mirror 29C is disposed to face the photoelectric read-out means 27 via the scanning line for efficiently reflecting the light 40, which is emitted by the recording belt 1 toward the mirror 29C, to the light input face of the light guide member 29B.

By way of example, as shown in FIGS. 6 and 7, the photomultiplier 28 has an electrode configuration generally called the venetian blind type. The photomultiplier 28 comprises a cylindrical body 28A, a photocathode 28b disposed along the inner surface of the body 28A to face a light receiving face 28a, and a multiplying section 28f disposed under the photocathode 28b and including a plurality (13 pieces in this embodiment) of plate-like dynodes 28c which are stacked via insulating members 28d, 28d secured by pins 28e, 28e. The dynodes 28c are respectively constituted by a conductive plate provided with a plurality of sections cut in a U-shape and bent to form a blind-like shape. A shield electrode 28g is secured by the pins 28e, 28e under the multiplying section 28f via the insulating members 28d, 28d, and an anode 28h is disposed inside of the shield electrode 28g. These electrodes are connected in one-to-one relation with terminals of a terminal group 28i disposed at the side end of the body 28A. The shield electrode 28g need not necessarily be provided.

Figure 8:
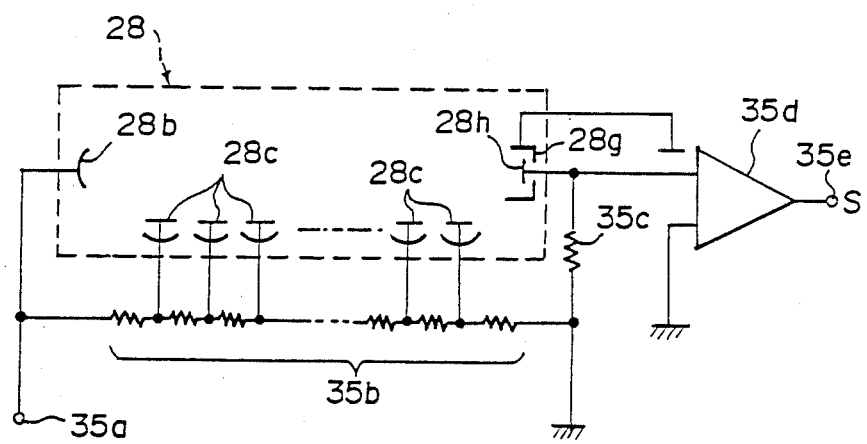
FIG. 8 is a circuit diagram showing the electric circuit for the photomultiplier shown in FIGS. 6 and 7, FIGS. 9A and 9B are elevational views showing another example of the recording and read-out unit employed in the radiation image recording and read-out apparatus in accordance with the present invention.

FIG. 8 shows an electric circuit for operating the photomultiplier 28 and obtaining a photoelectric output. In FIG. 8, similar elements are numbered with the same reference numerals with respect to FIGS. 6 and 7. The operations of the photomultiplier 28 will hereinbelow be described with reference to FIG. 8. A high negative voltage is applied to the photocathode 28b via a high negative voltage applying terminal 35a. The high negative voltage applied to the high negative voltage applying terminal 35a is divided by a bleeder resistance group 35b into voltages which are applied respectively to the dynodes 28c. The shield electrode 28g is grounded, and the anode 28h is connected with the bleeder resistance group 35b via a resistor 35c and with an amplifier 35d. Photoelectrons released from the photocathode 28b upon exposure to the light 40 emitted by the stimulable phosphor sheet 22 impinge upon the dynodes 28c in the course of advancement toward the anode 28h, and secondary electrons are thus released from the dynodes 28c. In this manner, the photoelectrons are sequentially amplified by the dynodes 28c, and the current thus obtained is fed to the amplifier 35d. The photoelectrically converted image information is thus obtained as analog electric signals (read-out image signals) S from an output terminal 35e of the amplifier 35d.

The portion of the recording belt 1 on which the image read-out has been finished is sent by the drive roller 45 to an erasing section 33. The erasing section 33 comprises a case 31, and a plurality of (by way of example, three) erasing light sources 32, 32, . . . constituted by fluorescent lamps or the like and disposed in the case 31. The erasing light sources 32, 32, . . . mainly produce erasing light having a wavelength within the stimulation wavelength range of the stimulable phosphor layer of the recording belt 1. The erasing light is irradiated to the overall image forming region of the recording belt 1 while the recording belt 1 is being conveyed, thereby to release radiation energy remaining on the stimulable phosphor layer of the recording belt 1 after the image read-out is finished. The recording belt portion on which the erasing has been finished at the erasing section 33 is conveyed to the image recording position for reuse in image recording.

As shown in FIG. 1, the output signals (read-out image signals) S generated by the amplifier (logarithmic amplifier) 35d are fed out of the recording and read-out unit 20, and digitized by an A/D converter 89. The digital read-out image signals D obtained in this manner and representing the radiation image of the object 11 are passed through an image processing apparatus 91 for carrying out gradation processing, frequency response processing or the like, and sent to an image reproducing apparatus 92. By way of example, the image reproducing apparatus 92 is constituted by a CRT, a light beam scanning recording apparatus or the like, and displays the image which the image signals D represent, i.e. the radiation image of the object 11 which was stored on the recording belt 1, or reproduces it as a hard copy.

As the erasing light sources 32, 32, . . . , tungsten-filament lamps, halogen lamps, infrared lamps, xenon flash lamps or the like as disclosed in U.S. Pat. No. 4,400,619 may be selected as well as the aforesaid fluorescent lamps. The erasing section 33 may also be composed of a surface type erasing light source such as a panel comprising light emitting diodes arrayed two-dimensionally or an EL (electroluminescence) plate, as well as a plurality of the erasing light sources 32, 32, . . . as mentioned above. Also, a lead plate 2 for shielding the radiation 12 is provided at the upper part in the recording and read-out unit 20, and therefore the radiation 12 produced by the radiation source 11 at the time of the image recording is prevented from impinging upon the recording belt 1 at the image read-out section 30 or the erasing section 33, or adversely affecting the image read-out section 30 or the erasing section 33.

Tomography will be described hereinbelow. Reverting to FIGS. 1 and 2, the recording and read-out unit 20 and the radiation source 10 are connected with each other by a connection means 60 which constitutes a part of the movement means 50. As shown in FIG. 2, the connection means 60 comprises vertical rods 51 and 52 parallel with each other, a horizontal rod 53 carried on the upper ends of the vertical rods 51 and 52 by rotation shafts 68, 68, and a horizontal rod 54 carried on the lower ends of the vertical rods 51 and 52 by rotation shafts 69, 69. The radiation source 10 is supported by the horizontal rod 53, and the recording and read-out unit 20 is supported by the horizontal rod 54. Also, the vertical rods 51 and 52 are supported on a base 66 at the middle between the horizontal rods 53 and 54 so that the vertical rods 51 and 52 are rotatable around a shaft 67B in the direction as indicated by the arrow B as shown in FIG. 1 and are rotatable around shafts 67C, 67C in the directions as indicated by the arrows C, C as shown in FIG. 2. The vertical rods 51 and 52 are connected to a drive means as will be described below. As shown in FIGS. 1 and 2 and in FIG. 3 which is a plan view taken in the direction as indicated by the arrow D of FIG. 1, the drive means comprises a rotatable table 71 positioned on the base 66, a male thread rod 72 positioned on the rotatable table 71, a female thread member 73 engaging with the male thread rod 72, and connection rods 74 and 75 positioned in a triangular form so that the base ends are rotatably connected with the female thread member 73 and the opposite ends are respectively connected with the vertical rods 51 and 52. The male thread rod 72 is supported by bearings 76 and 77 secured to the rotatable table 71 so that the male thread rod 72 may be rotated by a motor 78 in the direction as indicated by the arrow E in FIG. 1. The rotatable table 71 is rotated by a motor 79 in the direction as indicated by the arrow F. At the time the rotatable table 71 is thus rotated, the male thread rod 72 is rotated together with the rotatable table 71. However, the base ends of the connection rods 74 and 75 are rotatably connected with the female thread member 73, the connection rods 74 and 75 do not obstruct the rotation of the male thread rod 72.

Figure 3:
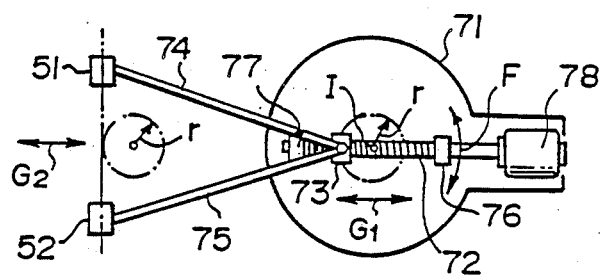
FIG. 3 is a partial plan view showing a part of the embodiment shown in FIG. 1, FIGS. 4 and 5 are an elevational view and a plan view showing the recording and read-out unit in the embodiment shown in FIG. 1, FIGS. 6 and 7 are a partially cutaway perspective view and a sectional side view showing the photomultiplier employed in the recording and read-out unit shown in FIG. 4.

The triangular form defined by the vertical rods 51 and 52, the female thread member 73, and the connection rods 74 and 75 which connect them does not change. Therefore, as shown in FIG. 3, when the rotatable table 71 is maintained stationary and the male thread rod 72 is rotated by the motor 78 to move the female thread member 73 linearly in the direction as indicated by the arrow G1, the connection means 60 is also linearly moved in the direction as indicated by the arrow G2. As a result, the radiation source 10 is moved, for example, in the directions as indicated by the arrows G3 and G4 in FIG. 1, and the recording and read-out unit 20 (and consequently the recording belt 1 at the image recording position) is moved in the directions as indicated by the arrows G5 and G6. The aforesaid linear rule and the geometric rule hold around an arbitrary tomographic layer 11T of the object 11 as shown in FIG. 1 between the radiation source 10 and the recording belt 1, and therefore linear path tomography can be carried out. Also, in the case where the same operation is carried out with the rotatable table 71 shown in FIG. 3 being rotated by 90°, the radiation source 10 is moved in the directions as indicated by the arrows H1 and H2 as shown in FIG. 2, and the recording belt 1 at the image recording position in the recording and read-out unit 20 is moved in the directions as indicated by the arrows H3 and H4. In this manner, it is possible to carry out linear path image recording in these directions. Also, in this case, the radiation source 10 and the recording belt 1 which are moved relative to each other satisfy the linear rule and the geometric rule around the arbitrary tomographic layer 11T. Also, as shown in FIG. 3, in the case where the female thread member 73 is deviated by a distance r from a center I of rotation of the rotatable table 71 and the rotatable table 71 is rotated in this condition, the female thread member 73 moves along a circle which has a radius r, and therefore the connection means 60 moves along a circle having a radius r. In this manner, it is possible to carry out circular path tomography. Also, in the case where the rotation of the male thread rod 72 in the direction as indicated by the arrow E and the rotation of the rotatable table 71 in the direction as indicated by the arrow F are combined with each other, it becomes possible to carry out tomography along various paths, for example, along a spiral path or a hypocycloidal path.

Legs 13a, 13a of the image recording table 13 are expanded and contracted by a known mechanism such as a hydraulic mechanism so that setting at the tomographic layer 11T of the object 11 can be effected as desired.

The radiation image read-out from the recording belt 1 carrying the tomographic image stored thereon and the reproduction of the radiation image (tomographic image) by use of the image signals obtained by the image read-out are carried out in the same manner as in the case of the ordinary image recording.

With the recording and read-out unit 20, the recording belt 1 is applied between the roller sections 43 and 46 spaced from each other by a distance approximately equal to the length of a single radiation image area, the image recording is carried out from above the recording belt 1, and the image read-out is carried out from below the recording belt 1. Therefore, all of the mechanisms of the recording and read-out unit 20 are housed in the small case 5 having the longitudinal and transverse dimensions slightly larger than the recording area for a single image (i.e. the single image in the ordinary image recording). With the recording and read-out unit 20 having such a configuration, the radiation image recording and read-out apparatus as a whole can be made small and light. A grid for absorbing the radiation scattered by the object 11, or a bucky device composed of the grid and a means for reciprocal movement of the grid may be provided above the recording belt 1 in the recording and read-out unit 20.

Also, in the aforesaid embodiment, the radiation source 10 and the recording and read-out unit 20 are mechanically connected with each other by the connection means 60. Instead, the radiation source 10 and the recording and read-out unit 20 may respectively be moved by a radiation source moving means and a recording and read-out unit moving means which are independent from each other, and the operations of the respective moving means may be controlled by control signals so that the radiation source 10 and the recording and read-out unit 20 are moved relative to each other to satisfy the linear rule and the geometric rule.

As mentioned above, the recording and read-out unit 20 is formed in the small case 5 slightly larger than the recording area for a single image. As such a small recording and read-out unit, different configurations may also be employed. Different examples of the small recording and read-out unit employed in accordance with the present invention will be described hereinbelow.

Figure 9A:
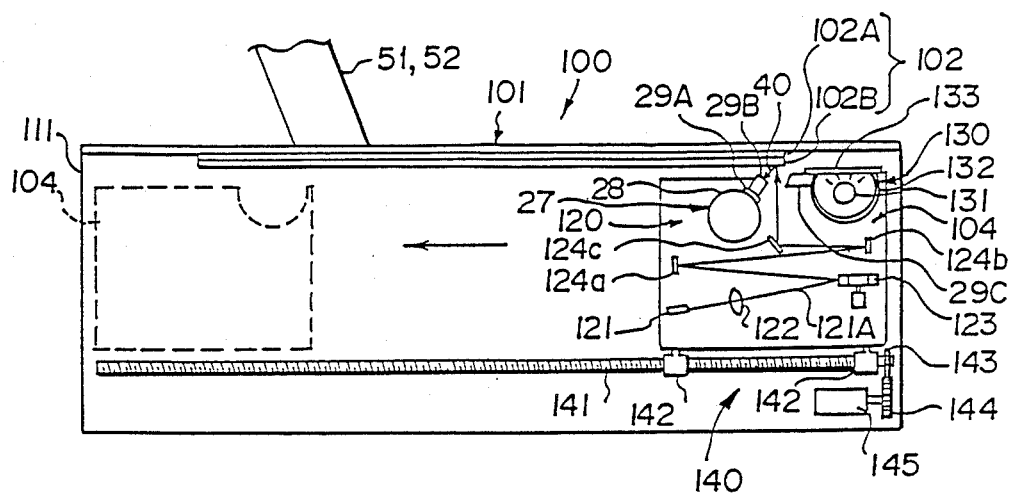
Figure 9B:
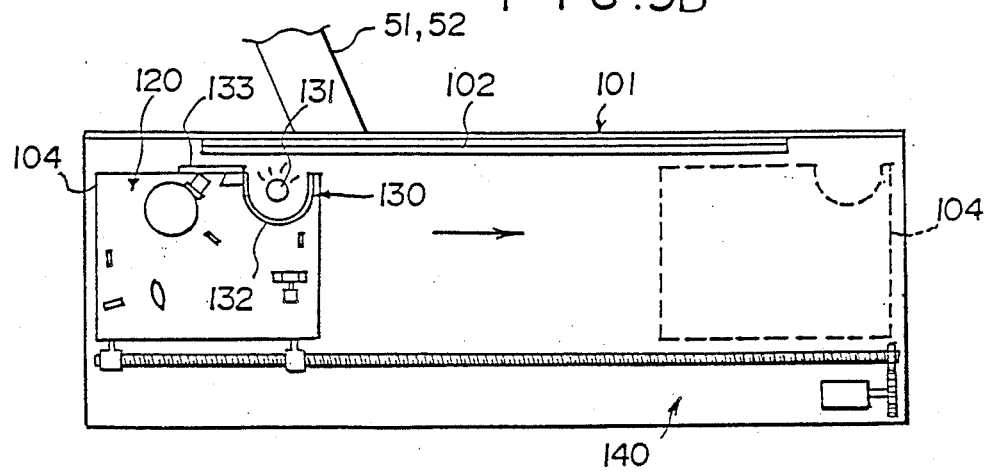

With reference to FIGS. 9A and 9B, a stimulable phosphor sheet 102 is secured horizontally at an image recording section 101 provided at the upper part of a case 111 of a recording and read-out unit 100. The case 111 has a size slightly larger than the size of the stimulable phosphor sheet 102. The stimulable phosphor sheet 102 is composed of a radiation-permeable substrate 102A and a stimulable phosphor layer 102B overlaid on the substrate 102B.

A read-out and erasing section 104 comprising a box 103, and an image read-out section 120 and an erasing section 130 integrally housed close to each other in the box 103 is provided below the stimulable phosphor sheet 102. The read-out and erasing section 104 is reciprocally moveable while facing the stimulable phosphor sheet 102 between the right end position (first position) as indicated by the solid line in FIG. 9A and the left end position (second position) as indicated by the solid line in FIG. 9B. In this embodiment, movement from the first position to the second position is referred to as forward movement, and movement from the second position to the first position is referred to as backward movement. Also, by way of example, a movement means 140 for reciprocally moving the read-out and erasing section 104 is composed of a screw rod 141 extending in the direction of movement of the read-out and erasing section 104, supporting members 142, 142 engaged with the screw rod 141, a gear 143 secured to the screw rod 141, a gear 144 meshing with the gear 143, and a motor 145 for rotating the gear 144 in the normal and reverse directions. The screw rod 141 is rotated by the motor 145 via the gears 143 and 144, thereby to move the supporting members 142, 142 forward and backward and carry out reciprocal movement of the read-out and erasing section 104.

The recording and read-out unit 100 may be utilized in the apparatus shown in FIG. 1 as a substitute for the recording and read-out unit 20. In this case, the stimulable phosphor sheet 102 is exposed to the radiation 12 produced by the radiation source 10 and passing through the object 11 in the same manner as in the aforesaid embodiment, thereby to store the radiation image on the stimulable phosphor layer 102B of the stimulable phosphor sheet 102. Also, the tomography is carried out in the same manner as in the aforesaid embodiment.

The image read-out section 120 is provided with a stimulating ray scanning means which comprises a stimulating ray source 121 constituted by a semiconductor laser or the like, a condensing lens 122 disposed in the optical path of stimulating rays 121A produced by the stimulating ray source 121, a rotating polygon mirror 123 as a light deflector for deflecting the stimulating rays 121A passing through the condensing lens 122 at an angle normal to the drawing sheet in FIG. 9A, thereby to scan the stimulating rays 121A in a main scanning direction on the stimulable phosphor sheet 102, and mirrors 124a, 124b and 124c for changing the optical path of the stimulating rays 121A. The stimulating rays 121A is made by the stimulating ray scanning means to repeatedly scan the stimulable phosphor sheet 102 in the main scanning direction. On the other hand, simultaneously with the scanning of the stimulating rays 121A is the main scanning direction, the read-out and erasing section 104 is conveyed by the movement means 140 at a predetermined speed leftward in FIG. 9A. As a result, the sub-scanning by the stimulating rays 121A is carried out, and almost the overall surface of the stimulable phosphor sheet 102 is exposed to the stimulating rays 121A. As the stimulable phosphor sheet 102 is exposed to the stimulating rays 121A, the exposed portion of the sheet 102 emits the light 40 in proportion to the stored radiation energy, and the emitted light 40 is detected by a photoelectric read-out means 27 of the image read-out section 120.

In this embodiment, the photoelectric read-out means 27 is formed in the same manner as in the recording and read-out unit 20 shown in FIGS. 4 and 5 and comprises the long photomultiplier 28, the filter 29A, the light guide member 29B, and the mirror 29C for reflecting the light 40 emitted by the stimulable phosphor sheet 102 toward the light receiving face of the light guide member 29B. When the image read-out by the photoelectric read-out means 27 has been finished, as shown in FIG. 9B, the read-out and erasing section 104 is conveyed rightward from its second position to its first position. An erasing means 130 is provided with an erasing light source 131 constituted by a fluorescent lamp or the like and extending in the main scanning direction, and a reflection plate 132 for reflecting the erasing light, that is radiated downward by the erasing light source 131, toward the surface of the stimulable phosphor sheet 102. Also, in this embodiment, the erasing light source 131 is normally turned on. Therefore, a moveable shutter 133 is provided so that it is disposed above the erasing light source 131 as shown in FIG. 9A to shield the erasing light at the time the image recording and the image read-out are carried out, and is retracted to the position above the photomultiplier 28 as shown in FIG. 9B to lay bare the erasing light source 131 only when the erasing is to be carried out. The moveable shutter 133 need not necessarily be provided in the case where the erasing light source 131 is turned on only when the erasing is to be carried out, and is turned off in the steps other than the erasing. As the read-out and erasing section 104 is moved in the manner as mentioned above, the erasing light source 131 irradiates the erasing light to the overall surface of the stimulable phosphor sheet 102. The erasing light source 131 mainly produces light having a wavelength within the stimulation wavelength range of the stimulable phosphor sheet 102, and radiation energy remaining on the sheet 102 after the image read-out therefrom has been carried out is released from the sheet 102 when the sheet 102 is exposed to the erasing light. The stimulable phosphor sheet 102 thus erased can be reused for image recording, and the read-out and erasing section 104 is returned to its first position.

With the recording and read-out unit 100 wherein a single stimulable phosphor sheet 102 is secured and held, and the image read-out and erasing are carried out by reciprocally moving the read-out and erasing section 104, the length of the recording and read-out unit 100 can be decreased nearly to the length of a single stimulable phosphor sheet 102.

In the recording and read-out unit 100, the stimulating rays 121A are scanned and the light 40 emitted by the stimulable phosphor sheet 102 is detected by the photomultiplier 28. However, as proposed in, for example, Japanese Patent Application No. 62(1987)-21957, (U.S. Ser. No. 145,180) it is also possible to linearly irradiate the stimulating rays to the stimulable phosphor sheet 102, and to detect the emitted light 40 by a line sensor. This also applies to the recording and read-out unit 20 shown in FIGS. 4 and 5, and the recording and read-out units as will be described later.

A further example of the recording and read-out unit employed in accordance with the present invention will hereinbelow be described with reference to FIG. 10. In a case 229 of a recording and read-out unit 200 shown in FIG. 10, a first wind-up shaft 222 and a second wind-up shaft 223 are provided in spaced and parallel relation to each other. The distance between the first wind-up shaft 222 and the second wind-up shaft 223 is adjusted to be slightly longer than the length of a single image area of the image recorded on a stimulable phosphor sheet 226 as will be described later. The first wind-up shaft 222 and the second wind-up shaft 223 are respectively rotated by motors 224 and 225 as the sheet feed means counter-clockwise and clockwise in FIG. 10. One end side of the stimulable phosphor sheet 226 capable of storing the radiation image thereon is wound around the first wind-up shaft 222. The stimulable phosphor sheet 226 is formed in the long strip-like shape by use of a flexible substrate. The other end side of the stimulable phosphor sheet 226 is supported by the second wind-up shaft 223 so that the sheet 226 can be wound up therearound. Also, the stimulable phosphor sheet 226 is applied between a roller 227 and rollers 228, 228 disposed between the first wind-up shaft 222 and the second wind-up shaft 223. The stimulable phosphor sheet 226 is positioned so that the flexible substrate substantially permeable to the radiation 12 faces up and the stimulable phosphor layer overlaid on the substrate faces down. With the recording and read-out unit 200, the recording of the radiation image of the object is carried out in the same manner as with the aforesaid recording and read-out units 20 and 100. Specifically, in the recording and read-out unit 200, an image recording section 280 is formed between the roller 227 and the rollers 228, 228.

An image read-out section 250 is provided below the stimulable phosphor sheet 226 in the vicinity of the second wind-up shaft 223. The image read-out section 250 is constituted by a stimulating ray source 251 which may be a semiconductor laser, a rotating polygon mirror 253 as a light deflector for reflecting and deflecting stimulating rays 252 produced by the stimulating ray source 251, a long mirror 259 for reflecting the deflected stimulating rays 252 so that the stimulating rays 252 one-dimensionally scans the stimulable phosphor sheet 228, specifically the stimulable phosphor layer thereof, the drive rollers 228, 228 composed of a pair of nip rollers for grasping the stimulable phosphor sheet 226 therebetween and acting as a sub-scanning means rotated at a predetermined speed, a long photomultiplier 254 disposed so that the light receiving face thereof extends along the scanning line (main scanning line) of the stimulating rays 252 on the stimulable phosphor sheet 226, and a long light guiding reflection mirror 255 extending along the long photomultiplier 254. In this embodiment, the photomultiplier 254 has the electrode configuration referred to as the box type. However, the photomultiplier of the type as shown in FIGS. 6 and 7 may also be employed. After a radiation image of the object is stored on the stimulable phosphor sheet 226 in the manner as mentioned above, the drive rollers 228, 228 are rotated to convey the stimulable phosphor sheet 226 at a predetermined speed rightward in FIG. 10. At this time, the second wind-up shaft 223 is rotated to wind up the stimulable phosphor sheet 226 therearound. An appropriate load has been given to the first wind-up shaft 222 by a known means (not shown) to maintain the stimulable phosphor sheet 226 in the tensioned condition. As the stimulable phosphor sheet 226 is thus conveyed, the stimulating ray source 251 and the rotating polygon mirror 253 are operated so that the stimulating rays 252 scan the stimulable phosphor sheet 226. The portion of the stimulable phosphor sheet 226 exposed to the stimulating rays 252 emits the light 40 carrying the radiation image stored on the stimulable phosphor sheet 226. The emitted light 40 is efficiently detected by the photomultiplier 254 directly or after being reflected by the light guiding reflection mirror 255. Simultaneously with the main scanning of the stimulating rays 252, the stimulable phosphor sheet 226 is conveyed in the sub-scanning direction, and consequently the detection of the light 40 emitted by the stimulable phosphor sheet 226 is carried out two-dimensionally.

The portion of the stimulable phosphor sheet 226 for which the image read-out has been finished in the manner as mentioned above is wound up around the second wind-up shaft 223. Also, a subsequent portion of the stimulable phosphor sheet 226 that has been wound around the first wind-up shaft 222 is fed to the position between the roller 227 and the drive rollers 228, 228, and it becomes possible to record a radiation image on said portion of the sheet 226 in the same manner as mentioned above. After the radiation image recording has thus been carried out over approximately the overall length of the stimulable phosphor sheet 226 and the sheet 226 that has been wound around the first wind-up shaft 222 has been delivered toward the second wind-up shaft 223, the motor 224 is operated to rotate the first wind-up shaft 222 counter-clockwise. Thus the stimulable phosphor sheet 226 on which the image read-out has been finished and which has been wound around the second wind-up shaft 223 is returned to the first wind-up shaft 222. At this time, the stimulable phosphor sheet 226 passes over an erasing section 260 provided between the roller 227 and the drive rollers 228, 228, and is subjected to image (residual image) erasing. By way of example, the erasing section 260 is constituted by a plurality of erasing light sources 262, 262, ... positioned below the stimulable phosphor sheet 226. The erasing light sources 262, 262, ... are constituted by fluorescent lamps or the like, and produce erasing light having a wavelength within the stimulation wavelength range for the stimulable phosphor of the stimulable phosphor sheet 226. The erasing light sources 262, 262, ... are turned on at the time the stimulable phosphor sheet 226 is returned to the first wind-up shaft 222. Upon exposure to the erasing light, the radiation energy remaining on the stimulable phosphor sheet 226 after the image read-out therefrom has been finished is released from the sheet 226. The erasing light is shielded by light shielding plates 262 and 263 so that it does not impinge upon the long photomultiplier 254 at the image read-out section 250. The light shielding plates 262 and 263 need not be provided in the case where the long photomultiplier 254 is turned off after the image read-out is finished.

In this manner, the stimulable phosphor sheet 226 on which the image (residual image) erasing has been effected to such an extent that the sheet 226 can be reused for the radiation image recording is stored around the first wind-up shaft 222. Therefore, the radiation image recording and the read-out can be repeated by use of the erased reusable stimulable phosphor sheet 226.

Figure 10:
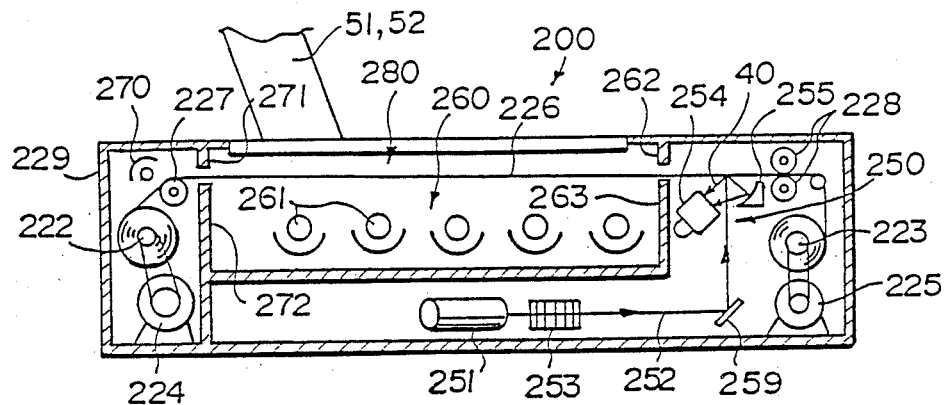
FIG. 10 is an elevational view showing a further example of the recording and read-out unit employed in the radiation image recording and read-out apparatus in accordance with the present invention.

In the embodiment shown in FIG. 10, a secondary erasing light source 270 for carrying out secondary erasing is provided between the first wind-up shaft 222 and the image recording section 280. The secondary erasing light source 270 is composed of a light source of the same type as the erasing light sources 261, 261, ... at the erasing section 260, and is turned on to irradiate the erasing light to the stimulable phosphor sheet 226 at the time the sheet 226 is delivered from the first wind-up shaft 222 for carrying out the radiation image recording. In the case where the stimulable phosphor sheet 226 has been stored around first wind-up shaft 222 without being used for a long period after being subjected to the image (residual image) erasing at the erasing section 260, the stimulable phosphor sheet 226 stores energy of radiations emitted by radioactive isotopes such as Ra226, which are contained as impurities in the stimulable phosphor, or energy of environmental radiations. These types of radiation energy undesirably stored on the stimulable phosphor sheet 226 cause noise in a radiation image recorded next on the stimulable phosphor sheet 226. Exactly prior to the image recording, such radiation energy is erased by exposing the stimulable phosphor sheet 226 to the secondary erasing light produced by the secondary erasing light source 270. The secondary erasing light is intercepted by light shielding plates 271 and 272 so that the sheet 226 prior to the image read-out is not exposed thereto.

In the embodiment shown in FIG. 10, the image recording and the image read-out are carried out alternately at the time the stimulable phosphor sheet 226 is wound up from the first wind-up shaft 222 to the second wind-up shaft 223. Instead, the image recording may first be carried out, and then the image read-out and the erasing may be carried out in the course of rewinding the stimulable phosphor sheet 226 from the second wind-up shaft 223 to the first wind-up shaft 222.

Figure 11:
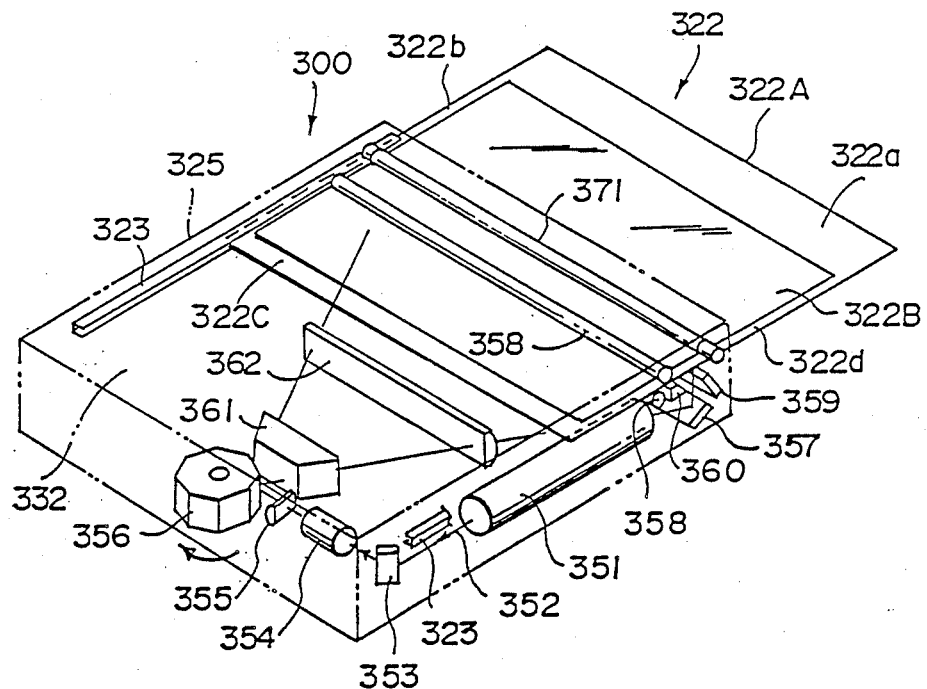
FIG. 11 is a schematic perspective view showing a still further example of the recording and read-out unit employed in the radiation image recording and read-out apparatus in accordance with the present invention.
Figure 12:
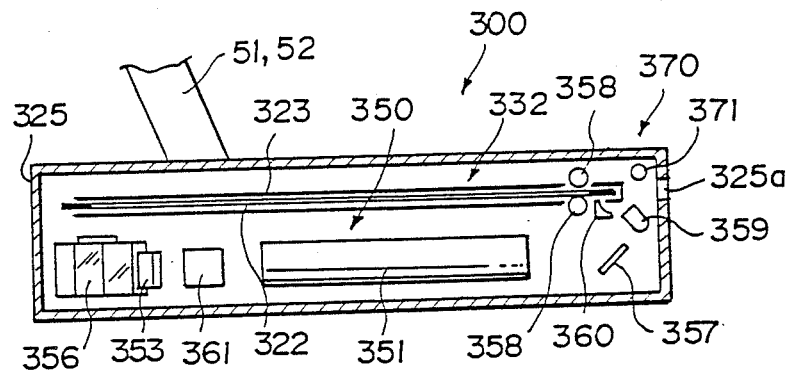
FIGS. 12 and 13 are partially cutaway elevational views showing the conditions of the recording and read-out unit shown in FIG. 11 in the course of image recording and in the course of image read-out.

A still further example of the recording and read-out unit employed in the radiation image recording and read-out apparatus in accordance with the present invention will hereinbelow be described with reference to FIGS. 11, 12 and 13. In a case 325 of a recording and read-out unit 300, a stimulable phosphor sheet 322 composed of, by way of example, a transparent plate-like substrate 322A and a stimulable phosphor layer 322B overlaid thereon is provided. The substrate 322A of the stimulable phosphor sheet 322 is formed to be larger than the stimulable phosphor layer 322B, and the portions of the substrate 322A around the stimulable phosphor layer 322B constitute holding portions 322a, 322b, 322c and 322d. In this embodiment, the stimulable phosphor sheet 322 is disposed so that the stimulable phosphor layer 322B comes under the substrate 322A, and is supported in the case 325 with the holding portions 322b and 322d being slideably supported on rails 323, 323. Specifically, the upper part of the case 325 including the rails 323, 323 is constituted as an image recording section 332 for holding the stimulable phosphor sheet 322 in the course of the radiation image recording. The longitudinal and transverse dimensions of the case 325 are adjusted to be slightly larger than those of the stimulable phosphor sheet 322. Also, as shown in FIG. 12, an end of the case 325 is provided with the elongated opening 325a which faces the edge face of the stimulable phosphor sheet 322. The regions of the case 325 outside of the region facing the image recording section 332 are lined with a radiation absorbing material such as a lead plate so that no fog is caused to arise on the stimulable phosphor sheet 322 by environmental radiations or the like other than the radiation used for the image recording.

With the recording and read-out unit 300, the recording of the radiation image of the object is carried out in the same manner as with the aforesaid recording and read-out units 20, 100 and 200, and the radiation image of the object 11 is stored on the stimulable phosphor sheet 322, specifically on the stimulable phosphor layer 322B formed on the lower surface side of the sheet 322.

An image read-out section 350 is provided below the stimulable phosphor sheet 322 in the case 325. The image read-out section 350 is provided with a stimulating ray source 351 constituted by a laser or the like, a mirror 353 for reflecting the stimulating rays 352 produced by the stimulating ray source 351, a beam expander 354 for adjusting the beam diameter of the stimulating rays 352 to a predetermined value, a cylindrical lens 355 for making the stimulating rays 352 impinge upon the mirror surface of a rotating polygon mirror 356 as will be described later so as to form a linear image, and the rotating polygon mirror 356 as a light deflector for reflecting and deflecting the stimulating rays 352. The image read-out section 350 is also provided with a long mirror 357 for reflecting the deflected stimulating rays 352 so that the stimulating rays 352 scan the stimulable phosphor layer 322B of the stimulable phosphor sheet 322 in one direction, and the drive rollers 358, 358 as the sub-scanning means composed of a pair of nip rollers for gripping the stimulable phosphor sheet 322 therebetween and rotated at a predetermined speed. The image read-out section 350 also comprises a long photomultiplier 359 positioned so that the light receiving face thereof extends along the scanning line (main scanning line) of the stimulating rays 352 on the stimulable phosphor sheet 322, and a long light guiding reflection mirror 360 extending along the long photomultiplier 359. Also, an fθ lens 361 and a cylindrical lens 362 are provided between the rotating polygon mirror 356 and the mirror 357, and the stimulating rays 352 are thereby made to converge to a predetermined beam diameter at every position on the stimulable phosphor sheet 322.

Figure 13:
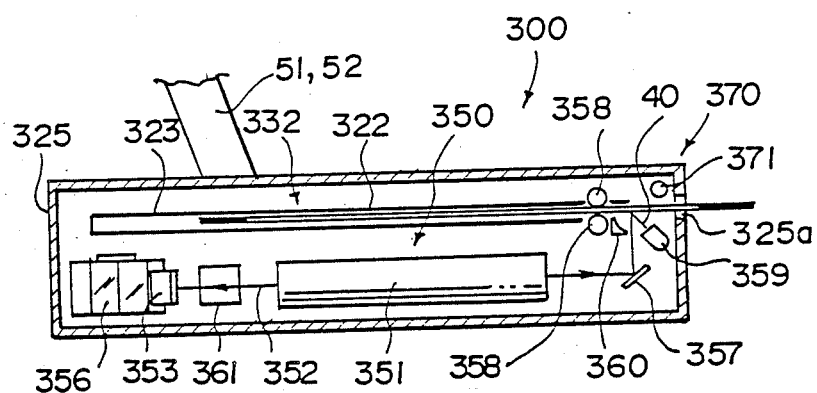

With reference to FIG. 13, after the radiation image of the object 11 has been stored on the stimulable phosphor sheet 322 in the manner as mentioned above, the drive rollers 358, 358 are rotated, and the stimulable phosphor sheet 322 is moved at a predetermined speed toward the opening 325a. In the course of the radiation image recording, the drive rollers 358, 358 grasp the holding portion 322a formed at one end of the stimulable phosphor sheet 322. Therefore, when the drive rollers 358, 358 are rotated after the image recording has been carried out, the stimulable phosphor sheet 322 can be immediately conveyed as mentioned above. Simultaneously with the conveyance of the stimulable phosphor sheet 322, the stimulating ray source 351 and the rotating polygon mirror 356 are activated, and the stimulating rays 352 scan on the stimulable phosphor sheet 322. The light 40 emitted by the stimulable phosphor sheet 322 is efficiently detected by the photomultiplier 359 directly or after being reflected by the light guiding reflection mirror 360. The scanning of the stimulating rays 352 in the main scanning direction is carried out in the manner as mentioned above and, at the same time, the stimulable phosphor sheet 322 is moved in the sub-scanning direction in the manner as mentioned above. Accordingly, the emitted light 40 is two-dimensionally read out from the stimulable phosphor sheet 322.

As shown in FIG. 13, when the stimulable phosphor sheet 322 is moved for the purpose of the subscanning, the stimulable phosphor sheet 322 is projected out of the case 325 through the opening 325a. Also, the stimulating rays 352 scan the stimulable phosphor sheet 322 at the position near the opening 325a. Therefore, at the time the image read-out has been finished, nearly the most part of the stimulable phosphor sheet 322 is projected out of the case 325. Accordingly, the case 325 need not be provided with a particular space for sub-scanning of the stimulable phosphor sheet 322, and may be formed in a size slightly larger than the size of the stimulable phosphor sheet 322.

At the time the image read-out has been finished in the manner as mentioned above, the holding portion 322c of the stimulable phosphor sheet 322 is grasped between the drive rollers 358, 358. Then, the drive rollers 358, 358 are rotated in the directions reverse to the directions of rotation at the time of the image read-out, and the stimulable phosphor sheet 322 is thereby returned to the image recording section 332 inside of the case 325. At this time, the stimulable phosphor sheet 322 passes over an erasing section 370 provided in the vicinity of the opening 325a in the case 325, and is subjected to the image (residual image) erasing. The erasing section 370 is constituted by an erasing light source 371 provided above the stimulable phosphor sheet 322.

In this manner, the stimulable phosphor sheet 322 on which the image (residual image) has been erased to such an extent that the stimulable phosphor sheet 322 becomes reusable for the radiation image recording is housed in the case 325. Therefore, the image recording and the image read-out can be repeated by use of the stimulable phosphor sheet 322. The erasing section 370 may also be constituted by disposing a surface type erasing light source, which may be an EL (electroluminescence) plate, so that it faces the stimulable phosphor sheet 322 at the image recording position from below, i.e. from the side of the stimulable phosphor layer 322B. In this case, the substrate 322A of the stimulable phosphor sheet 322 need not necessarily be formed of a transparent material. With this configuration, the aforesaid secondary erasing can be carried out easily by the utilization of the surface type erasing light source.

We claim:

1. A radiation image recording and read-out apparatus which comprises:
   (i) a radiation source for irradiating a radiation toward an object,
   (ii) a recording and read-out unit provided with:
      (a) a case for housing therein a stimulable phosphor sheet and having longitudinal and transverse dimensions approximately equal to the longitudinal and transverse dimensions of a single image recording area on said stimulable phosphor sheet,
      (b) an image recording section for holding said stimulable phosphor sheet in said case at an image recording position exposed to the radiation passing through said object, and having a radiation image of said object stored on said stimulable phosphor sheet,
      (c) an image read-out section provided in said case for exposing said stimulable phosphor sheet carrying said radiation image stored thereon to stimulating rays which cause said stimulable phosphor sheet to emit light in proportion to the stored radiation energy, and photoelectrically detecting the emitted light to obtain image signals, and
      (d) an erasing section provided in said case for releasing the radiation energy remaining on said stimulable phosphor sheet, for which the detection of said emitted light has been carried out, before the image recording is carried out on said stimulable phosphor sheet, and
   (iii) a movement means for moving said recording and read-out unit and said radiation source so that said stimulable phosphor sheet at said image recording position approximately satisfies the linear rule and the geometric rule with respect to said radiation source around an arbitrary tomographic layer.

2. An apparatus as defined in claim 1 wherein said stimulable phosphor sheet is shaped in an endless belt-like form, said stimulable phosphor sheet in the endless belt-like form is held at said image recording position by being applied around two sets of roller sections which are spaced from each other by a distance approximately equal to the length of a single image area, and in the course of feeding the image-recorded portion of said stimulable phosphor sheet out of said image recording position and feeding a different portion of said stimulable phosphor sheet to said image recording position, said stimulating rays are scanned in a sub-scanning direction by the movement of said stimulable phosphor sheet, whereby the detection of said light emitted by sad stimulable phosphor sheet is carried out.

3. An apparatus as defined in claim 1 wherein said stimulable phosphor sheet is secured at said image recording position, said image read-out section and said erasing section are provided on a moveable body for movement along the surface of said stimulable phosphor sheet, and said stimulating rays are scanned in a subscanning direction by the movement of said moveable body, thereby to carry out the detection of said light emitted by said stimulable phosphor sheet, and the image erasing is carried out by the movement of said moveable body.

4. An apparatus as defined in claim 1 wherein said stimulable phosphor sheet is formed as a long strip-like flexible sheet, one end and the other end of said stimulable phosphor sheet are respectively wound around a first wind-up shaft and a second wind-up shaft, whereby said stimulable phosphor sheet is applied at the image recording position between said first wind-up shaft and said second wind-up shaft, and said stimulating rays are scanned in a subscanning direction by the wind-up movement of said stimulable phosphor sheet between said first wind-up shaft and said second wind-up shaft, whereby the detection of said light emitted by said stimulable phosphor sheet is carried out.

5. An apparatus as defined in claim 1 wherein an opening through which said stimulable phosphor sheet is to be passed is formed at one end of said case which one end faces an edge of said stimulable phosphor sheet, and said stimulating rays are scanned in a subscanning direction by such movement of said stimulable phosphor sheet that said stimulable phosphor sheet is projected out of said case through said opening from said image recording section, whereby the detection of said light emitted by said stimulable phosphor sheet is carried out.

* * * * *